United States Patent
Gauthier et al.

(10) Patent No.: US 10,493,438 B2
(45) Date of Patent: Dec. 3, 2019

(54) METHOD TO PURIFY OLEFIN-CONTAINING HYDROCARBON FEEDSTOCKS

(75) Inventors: William J. Gauthier, Houston, TX (US); Olivier Miserque, Mont-Saint-Guibert (BE); George Vulpescu, Ciply (BE); Francine Genin, Nivelles (BE); Kai Hortmann, Dilbeek (BE); Jean-Pierre Dath, Beloeil (BE)

(73) Assignee: TOTAL RESEARCH & TECHNOLOGY FELUY, Seneffe (BE)

( * ) Notice: Subject to any disclaimer, the term of this patent is extended or adjusted under 35 U.S.C. 154(b) by 371 days.

(21) Appl. No.: 13/141,283

(22) PCT Filed: Dec. 22, 2009

(86) PCT No.: PCT/EP2009/067803
§ 371 (c)(1),
(2), (4) Date: Sep. 7, 2011

(87) PCT Pub. No.: WO2010/072789
PCT Pub. Date: Jul. 1, 2010

(65) Prior Publication Data
US 2012/0046512 A1    Feb. 23, 2012

(30) Foreign Application Priority Data

Dec. 22, 2008 (EP) .................... 08172528

(51) Int. Cl.
*B01J 23/755* (2006.01)
*C07C 7/167* (2006.01)
(Continued)

(52) U.S. Cl.
CPC ............. *B01J 23/755* (2013.01); *C07C 7/167* (2013.01); *B01J 35/0026* (2013.01);
(Continued)

(58) Field of Classification Search
USPC ......... 585/258–262, 275–277, 809; 502/325, 502/259, 335
See application file for complete search history.

(56) References Cited

U.S. PATENT DOCUMENTS 2,077,421 A * 4/1937 Lazier .......................... 549/503
3,258,431 A * 6/1966 Ford et al. ...................... 502/74
(Continued)

FOREIGN PATENT DOCUMENTS

CN    101185826 A    5/2008
EP    0308569 A1    3/1989
(Continued)

OTHER PUBLICATIONS

C. H. Bartholomew and R. B. Pannell, "The Stoichiometry of Hydrogen and Carbon Monoxide Chemisorption on Alumina- and Silica-Supported Nickel," Apr. 14, 1980, Journal of Catalysis 65, pp. 390-401.*
(Continued)

*Primary Examiner* — Tam M Nguyen
(74) *Attorney, Agent, or Firm* — Albert Shung

(57) ABSTRACT

A process for purifying an olefin-containing hydrocarbon feedstock comprising the steps of:
(a) passing the said hydrocarbon feedstock in the presence of hydrogen over a first catalyst bed material comprising nickel deposited on a support material wherein said nickel is present as both nickel oxide and metallic nickel
(b) recovering the feedstock having a substantially reduced acetylenics (in particular methylacetylene) and allenes (in particular propadiene) content.

23 Claims, 1 Drawing Sheet

(51) Int. Cl.
*B01J 35/00* (2006.01)
*B01J 35/10* (2006.01)

(52) U.S. Cl.
CPC ........ *B01J 35/1014* (2013.01); *B01J 35/1019* (2013.01); *C07C 2523/755* (2013.01); *Y02P 20/52* (2015.11)

(56) References Cited

U.S. PATENT DOCUMENTS

| | | | |
|---|---|---|---|
| 3,444,256 A | 5/1969 | Engelhard et al. | |
| 3,755,488 A | 8/1973 | Johnson et al. | |
| 3,792,981 A | 2/1974 | Hettick et al. | |
| 3,812,057 A | 5/1974 | Morgan et al. | |
| 3,887,632 A | 6/1975 | Liakumovich et al. | |
| 3,912,789 A | 10/1975 | Frevel et al. | |
| 3,932,534 A * | 1/1976 | Fukunaga et al. | 568/814 |
| 4,020,119 A | 4/1977 | Johnson et al. | |
| 4,257,877 A * | 3/1981 | Mahendroo | 208/144 |
| 4,425,255 A | 1/1984 | Toyoda et al. | |
| 4,440,956 A | 4/1984 | Couvillion | |
| 5,157,201 A * | 10/1992 | Norris | 585/820 |
| 5,332,705 A | 7/1994 | Huang et al. | |
| 5,478,791 A * | 12/1995 | Baldauf et al. | 502/337 |
| 5,679,241 A * | 10/1997 | Stanley et al. | 208/92 |
| 5,985,131 A * | 11/1999 | Gupta et al. | 208/57 |
| 6,163,218 A | 12/2000 | Hashimoto et al. | |
| 6,673,743 B2 * | 1/2004 | Lok | 502/337 |
| 6,717,022 B2 * | 4/2004 | Ryu et al. | 585/261 |
| 7,026,269 B2 * | 4/2006 | Vanoppen et al. | 502/327 |
| 7,408,089 B2 * | 8/2008 | Ryu | 585/259 |
| 2004/0030207 A1 | 2/2004 | Ryu et al. | |
| 2006/0235254 A1 * | 10/2006 | Gartside et al. | 585/664 |
| 2007/0142683 A1 | 6/2007 | Frenzel et al. | |
| 2009/0318739 A1 * | 12/2009 | Liu et al. | 585/276 |

FOREIGN PATENT DOCUMENTS

| | | |
|---|---|---|
| EP | 0648720 A1 | 4/1995 |
| EP | 2006011 A1 | 12/2008 |
| FR | 1487588 A | 7/1967 |
| GB | 646408 A | 11/1950 |
| GB | 800320 A | 8/1958 |
| GB | 861995 A | 3/1961 |
| GB | 920269 A | 3/1963 |
| GB | 2162194 A | 1/1986 |
| GB | 2242199 A | 9/1991 |
| JP | S6150929 A | 3/1986 |

OTHER PUBLICATIONS

Office Action issued in Chinese Application No. 200980157209.6 dated May 14, 2014, and an English translation thereof (17 pages).

* cited by examiner

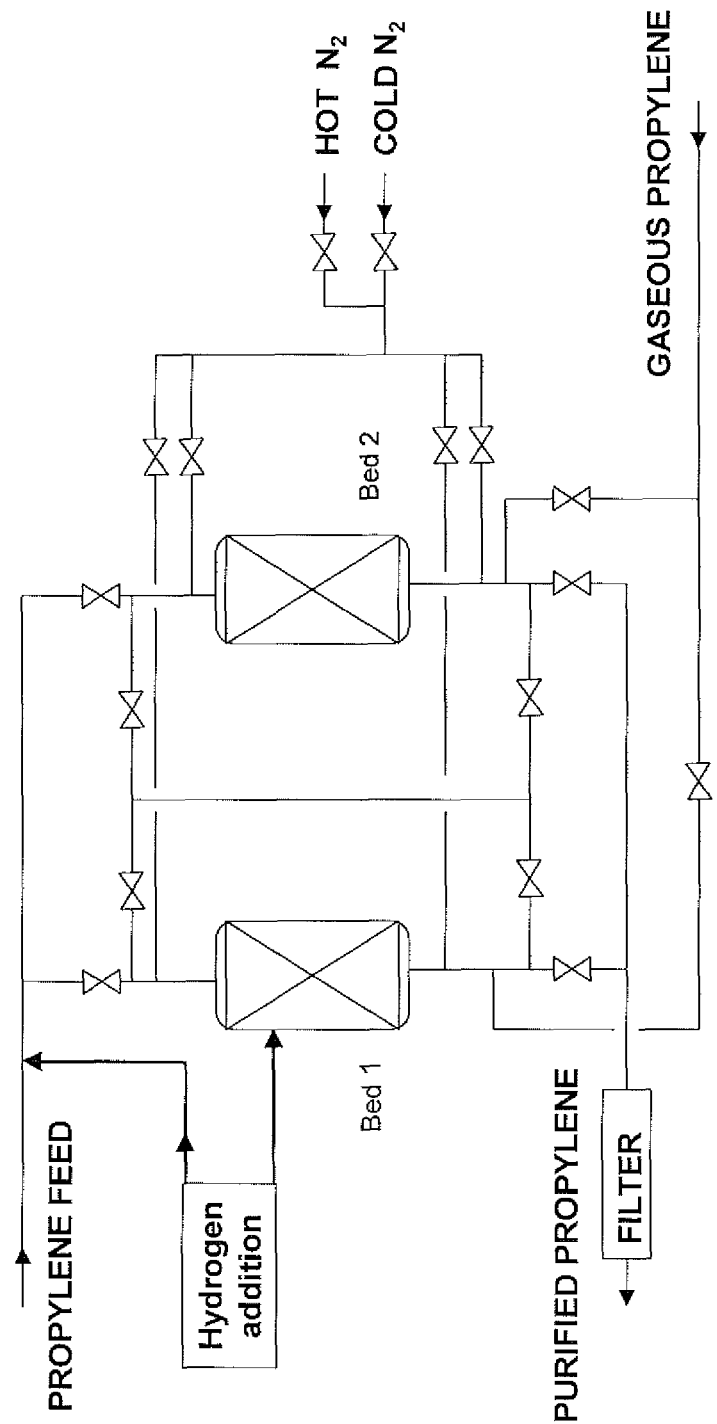

METHOD TO PURIFY OLEFIN-CONTAINING HYDROCARBON FEEDSTOCKS

CROSS-REFERENCE TO RELATED APPLICATIONS

This application claims the benefit of PCT/EP2009/067803, filed Dec. 22, 2009, which claims priority from EP 08172528.5, filed Dec. 22, 2008.

FIELD OF THE INVENTION

The present invention relates to a process for the reduction of acetylenics and diolefins, in particular allenes e.g. propadiene, in olefin-containing hydrocarbons to levels previously not obtainable. More particularly, the present invention relates to a process for the reduction of acetylenics and diolefins in propylene feedstocks.

BACKGROUND OF THE INVENTION

As is well known, olefins, in particular ethylene and propylene, are used to produce numerous types of intermediate and end products, which are predominantly polymeric materials. Commercial production of olefins is generally carried out by thermal cracking of hydrocarbon feedstocks containing ethane, propane, liquid naphtha or mixtures thereof.

Unfortunately, due to the very high temperatures involved, these commercial olefin producing processes also yield a substantial amount of the less desired acetylenic (alkyne) impurities such as acetylene, methylacetylene and $C_4$ alkynes, and also diolefins, in particular allenes such as propadiene, which contaminate the target olefin streams. Propylene and ethylene feeds, for example, may contain up to several weight percent of methylacetylene and propadiene (known as MAPD), when directly obtained from the cracking process.

Other typical processes to obtain olefins, such as fluid catalytic cracking, Methanol to Olefins (MTO) and Olefin Conversion Process (OCP), may also give rise to feedstocks having high and fluctuating amounts of acetylenic impurities, predominantly methylacetylene, and diolefins, in particular allenes such as propadiene.

These same olefins are subsequently catalytically converted to a multitude of polymeric products on a large scale. Various types of catalysts can be used for the polymerisation process. In particular, metallocene catalysts are becoming increasingly prevalent in industry. Unfortunately, these new generation catalysts are, as well as being much more expensive, also very sensitive. Their activities are severely limited by impurities present in the hydrocarbon or hydrogen feed. It is well known that acetylenics and allenes are extremely strong poisons for polymerisation catalysts, particularly metallocenes.

For a person skilled in the art, an obvious solution to remove acetylenic impurities and allenes from olefin-containing hydrocarbon feedstocks is by distillation, since for example, methylacetylene and propadiene have boiling points of −23° C. and −34° C., which are sufficiently different from the boiling point of olefins (propylene −47° C., ethylene −169° C.) and therefore easily removed. However, installing a distillation tower not only implies high capital costs, but also expensive operating costs, and is thus only suitable for purifying olefins on an extremely large scale.

Several other methods are known for separating unsaturated hydrocarbon impurities from hydrocarbon feedstocks. These include, for instance, cryogenic distillation, liquid adsorption, membrane separation and pressure swing adsorption in which adsorption occurs at a higher pressure than the pressure at which the adsorbent is regenerated. Liquid adsorption is a common technique for the separation of impurities and alkenes from gaseous mixtures containing molecules of similar size, e.g. nitrogen or methane. However, both techniques have disadvantages such as high capital cost and high operating expenses. For example, liquid adsorption techniques suffer from solvent loss and need a complex solvent make-up and recovery system.

Acetylenic impurities, but also diolefins e.g. allenes, are most commonly reduced in the hydrocarbon feedstock by hydrogenation in the presence of a hydrogenation catalyst and hydrogen. However, not only is the reaction highly exothermic, but also the rate of hydrogenation of olefins to paraffins is up to 100 times faster than that of acetylenes to olefins, for example, methylacetylene to propylene. In spite of significant progress over the years, this process has significant shortcomings such as the appearance of side products such as a "green oil" and propane, and deposition of carbonaceous residues and other impurities such as arsine or carbonyl sulphide, which deactivate the catalyst. Therefore, acetylene hydrogenation processes for treating liquid or liquefiable olefins and diolefins, such as allenes, typically include an oxygenation step or a "burn" step to remove the deactivating carbonaceous residues from the catalyst, followed by a hydrogen reduction step to reactivate the hydrogenation catalyst. For example, see U.S. Pat. No. 3,755,488 to Johnson at al., U.S. Pat. No. 3,792,981 to Hettick et al., U.S. Pat. No. 3,812,057 to Morgan and U.S. Pat. No. 4,425,255 to Toyoda. However, U.S. Pat. Nos. 3,912,789 and 5,332,705 state that by using selected hydrogenation catalysts containing palladium, at least partial regeneration can be accomplished using a hydrogenation step alone at high temperatures of 316° to 371° C. and in the absence of an oxygenation step. However, these are cost intensive, inefficient, unselective hydrogenation processes, not appropriate for obtaining the purity levels necessary for polymerisation, preferably down to the ppb range. Furthermore, they do not simultaneously remove the other impurities present in the propylene feed, such as carbonyl sulphide, arsine, antimony compounds such as antimony hydride, and carbon monoxide.

Beside palladium and modified palladium, copper with some additives can be used also as a catalyst for selective hydrogenation as seen in U.S. Pat. Nos. 3,912,789 and 4,440,956. Kokai JP Number 50929-1968 describes a method of purifying vinyl compounds containing up to about 10 percent by weight of acetylenic compounds. In this method, acetylenic compounds were described as being adsorbed on an adsorption agent of 1-valent and/or O-valent copper and/or silver supported on inert carrier such as delta alumina, silica or active carbon. Separations described included 1000 ppm ethyl acetylene and 1000 ppm vinyl acetylene from liquid 1,3-butadiene, 100 ppm acetylene from ethylene gas, 100 ppm methylacetylene from propylene gas, and 50 ppm phenyl acetylene from liquid styrene (vinylbenzene). Each application used fresh adsorption agent and only a short time of one hour on stream at mild conditions of temperature and pressure. Such limited applications were likely because it is well known that acetylene and these acetylene compounds react with copper and/or silver to form copper acetylide or silver acetylide. Both the acetylide of copper and silver are unstable compounds.

Because they are explosive under some conditions, their possible formation presents safety problems in operation and in handling adsorbent containing such precipitates. A current commercial process employs a copper based catalyst in the presence of hydrogen.

The use of metallic nickel/nickel oxide sorbents is known to reduce the level of certain impurities. These are carbonyl sulphide, arsine, antimony compounds such as antimony hydride, and carbon monoxide using nickel/nickel oxide materials (See EP 0 308 569, GB 2162194, GB 2242199, EP 0 648 720 and EP 2 006 011). However, until now these have never been used in the presence of hydrogen and have certainly not been used as hydrogenation catalysts.

A method to reduce the content of acetylenics and diolefins (in particular allenes e.g. propadiene) in an olefin-containing hydrocarbon feedstock is needed with minimal capital investment, whilst removing other impurities from the feedstock.

It is a further aim to convert the acetylenics and diolefins (in particular allenes e.g. propadiene) selectively over the olefins contained in the hydrocarbon feedstock.

It is an aim to reduce the acetylenics and diolefins (in particular allenes e.g. propadiene) content of olefin-containing hydrocarbon feedstocks more efficiently.

It is also an aim to provide olefin-containing hydrocarbon feedstocks suitably purified for catalytic polymerization, in particular suitable for metallocene-catalysed polymerisation.

SUMMARY OF THE INVENTION

A process for purifying an olefin-containing hydrocarbon feedstock comprising the steps of:
(a) passing the said hydrocarbon feedstock in the presence of hydrogen over a first catalyst bed material comprising nickel deposited on a support material wherein said nickel is present as both nickel oxide and metallic nickel
(b) recovering the feedstock having a substantially reduced acetylenics and diolefins (in particular allenes e.g. propadiene) content.

The invention also relates to the use of a catalyst bed material comprising nickel deposited on a support material wherein said nickel is present as both nickel oxide and metallic nickel to reduce the content of acetylenics and diolefins (in particular allenes e.g. propadiene) in hydrocarbon feedstocks to levels suitable even for metallocene-catalysed polymerisations.

The use of a catalyst bed material comprising nickel deposited on a support material wherein said nickel is present as both nickel oxide and metallic nickel to purify olefin-containing hydrocarbon feedstock in the presence of hydrogen is also claimed.

This surprisingly results in feedstocks wherein the acetylenics and diolefins (in particular allenes) are substantially removed by converting a majority of said impurities into olefins. In particular, methylacetylene and propadiene are hydrogenated.

This is important since acetylenics and diolefins (in particular allenes e.g. propadiene) are known to cause reactor blockage during polymerisation of olefins such as ethylene and propylene, due to catalyst deactivation and thermal runaways. This translates as unscheduled reactor shutdowns and increased costs for replacing the deactivated catalysts, in the case of metallocene catalysts.

Surprisingly, despite the rate of hydrogenation being faster for olefins than for acetylenics, it was observed that using the nickel/nickel oxide catalyst bed material, acetylenics were hydrogenated more preferentially than expected, whilst still maintaining good levels of removing other impurities from the propylene feed by ab- and adsorption.

BRIEF DESCRIPTION OF DRAWINGS

FIG. 1 shows a schematic representation of the propylene purification process.

DETAILED DESCRIPTION OF THE INVENTION

The present invention relates to the conversion of acetylenics and diolefins (in particular allenes e.g. propadiene) in olefin-containing hydrocarbon feeds by hydrogenation. While the subsequent discussion will describe the invention in terms of treating propylene-containing feeds, the present invention may be applicable to the treatment of hydrocarbon feeds containing other olefins e.g. ethylene, propylene, butenes, pentenes, hexenes, octenes or any combinations thereof. However, due to propylene's physical properties, the process is preferably applied to the purification of propylene.

The Catalyst Bed Material

For the purposes of the present invention, the nickel/nickel oxide material is referred to generally as a catalyst bed material.

The catalyst bed material of the present invention comprises nickel deposited on a support material, the nickel being present both as metallic nickel and as nickel oxide. Silica, silico-aluminas, alumina, kieselguhr, zeolites and other similar materials, whether amorphous or crystalline, can be utilised as the support. The total weight of nickel oxide and metallic nickel may represent up to about 80 wt. % of the catalyst bed material, with the provision that metallic nickel should not represent less than 6 wt. %, preferably not less than 10 wt. %, nor more than 50 wt. % of the catalyst bed material. Preferably, the total weight of nickel oxide and metallic nickel represents from 10 to 80 wt. %, preferably of 40 to 70 wt. %, of the catalyst bed material, and the catalyst bed material includes 20 to 90 wt. %, preferably 30 to 60 wt. % of the support material. Advantageously, the weight ratio of metallic nickel to nickel oxide is of about 0.4 to about 2.0, and the catalyst bed material comprises from about 30 to about 60 wt. % of support material. More advantageously, the weight ratio of metallic nickel to nickel oxide is from 0.4 to 2.0 (even more advantageously from 0.4 to 1.0), with the provision that metallic nickel should neither represent less than 6 wt. %, nor more than 50 wt. % of the catalyst bed material, and the catalyst bed material comprises from 40 to 70 wt. % of metallic nickel and nickel oxide (even more advantageously from 45 to 55 wt. %) and from 30 to 60 wt. % of support material (even more advantageously from 45 to 55 wt. %). When carrying out the process of the invention with a catalyst bed material outside this definition, the results obtained may no longer be satisfactory, although some of the unsaturated impurities will still be hydrogenated. Whilst not wishing to be bound by any theory, the Applicant believes that larger crystallites are formed if the nickel to nickel oxide ratio is higher, thus leading to a lower efficiency; similarly, an excessive total nickel content tends to lower the specific surface and consequently the efficiency, while a too low total nickel content would lead to an insufficient capacity for the reactants.

The nickel can be deposited on the support by any of the several methods well known to those skilled in the art. For example, nickel can be deposited on the support by dissolving nickel nitrate in water, mixing the solution with the support and precipitating the nickel, for example in the form of nickel carbonate, and subsequently washing, drying and calcining the precipitate. The nickel deposited in this manner is then partially reduced by means of hydrogen to form metallic nickel, the remainder being in the form of nickel oxide.

In general, the size of the nickel crystallites after reduction is from 1 to 100 nm, preferably 1 to 50 nm, more preferably 1 to 30 nm, even more preferably 1 to 10 nm and most preferably 1 to 2 nm. The size of the nickel crystallites depends on the extent of reduction carried out. In fact, if the degree of reduction is increased, the size of the crystallites is increased but the catalyst bed material obtained does not have the desired properties. On the other hand, if the degree of reduction is too low, the crystallites still have good dimensions but the quantity of nickel available in this case is too small to ensure successful purification of the hydrocarbon feedstock.

The specific surface area of the catalyst bed material obtained after reduction is from 10 to 400 $m^2/g$, preferably from 100 to 200 $m^2/g$.

The particle size of the catalyst bed material depends especially on the pressure drop allowed in the reactor; it has been noted, however, that it is advantageous to use the catalyst bed material in finely divided form. Preferably, the particle diameter of this material when spherical does not exceed about 3.5 mm and is most preferably from 1 to 2.5 mm. When cylindrical particles are used, they preferably have a diameter of from 1 to 2 mm and a length of from 3 to 8 mm. Trilobes of similar size may also be used.

The catalyst bed material is usually prepared ex situ and stored either under a convenient saturated liquid hydrocarbon, like cyclohexane or dodecane, or under a non-oxidizing atmosphere like $N_2$. It can also be protected by deposition of a carbon dioxide layer on the surface, said layer protecting the catalyst bed material from air, thus allowing easy handling.

It has been found that propylene adsorbs onto the catalyst bed material when contacted with the feedstocks, and that the propylene adsorption reaction, occurring during start-up, is exothermic. Under certain conditions, and particularly when the catalyst bed material is stored under a non-oxidizing atmosphere, the temperature rise may be very important. More particularly the temperature at the surface of the material may be much higher than that measured with a thermocouple, and the catalyst bed material may thus be damaged. In addition, the high temperatures trigger undesired side-reactions, more particularly propylene dimerisation and trimerisation. The dimers are hexenes, which can copolymerise with propylene. If this purified propylene stream is then used for polymerisations, these by-products can break the regularity of the linear chain of, for example, isotactic polypropylene or otherwise cause other process difficulties. As a result, the copolymer has a lower crystallinity than polypropylene, and thus a lower melting point; its mechanical resistance is also lower. More seriously, during polymerisation these dimers also act as retarders by blocking active sites on the catalyst, thereby significantly reducing productivity. Also, such impurities typically reduce the polymerisation rate of propylene polymerisations thus leading to reduced economic advantage.

The Applicants have found that an excessive increase in the temperature of the catalyst bed material can be avoided by conditioning it before use. Conditioning can be carried out by passing an inert gas flow containing a minor amount of at least one light olefin, preferably propylene, in a concentration of from 0.1 to 5 vol %, over said material. The inert gas is usually nitrogen, which should contain the least possible amount of oxygen. It is preferable to begin the conditioning procedure by passing essentially pure inert gas over the material. The conditioning step is preferably carried out at about atmospheric pressure, at or below ambient temperature. It is continued until the propylene concentration at the outlet equals that introduced. It is also possible to monitor the passage of an exotherm, shown by thermocouples introduced within the catalyst bed material.

It is known that, when the catalyst bed material is prepared ex situ and protected by a monolayer of carbon dioxide (believed to be sorbed onto the nickel surface), the said material must be pre-treated prior to its conditioning by passing an initial inert gas (containing the least possible amount of oxygen) over it at a temperature of from about 150° C. to about 350° C., preferably at about 250° C. and preferably at about atmospheric pressure. This is then preferably followed by passing a mixture of inert gas and hydrogen containing an increasing concentration of hydrogen over the said material (to remove any oxygen possibly that may have been sorbed despite all precautions), before purging it free of hydrogen with an inert gas flow at about 250° C.

Treatment of the Olefin-Containing Hydrocarbon Feedstock

In polyolefin production, the hydrocarbon feedstock generally comprises more than 75 wt. % of olefins, preferably propylene, more particularly from 85 to 99.99 wt. %.

In one embodiment of the present invention, before the olefin-containing hydrocarbon feedstock is passed over the catalyst bed material, hydrogen is introduced into the hydrocarbon feedstock. Preferably, the desired final content of acetylenics and diolefins (in particular allenes e.g. propadiene) impurities is less than 10 ppm, more preferably less than 5 ppm and even more preferably less than 1 ppm, depending on the intended use of the purified olefin-containing hydrocarbon feedstock.

In order to substantially convert the acetylenics and allenes (in particular allenes e.g. propadiene), the molar ratio of hydrogen to total acetylenics and allenes is preferably up to 1 to 1500, more preferably up to 1 to 1000, even more preferably 1 to 750, and most preferably up to 1 to 500. However, this is pressure and temperature dependent. Higher pressures require lower molar ratios of hydrogen to acetylenics and allenes. The exact amount of ppm mol hydrogen will depend upon the content of acetylenics and allenes to be hydrogenated. Merely as an example: at 17 barg and 20° C., if the hydrocarbon feedstock contains a total of 5 ppm of acetylenics and allenes, a concentration of up to 2500 ppm of hydrogen will most preferably be introduced into the feedstock prior to passing it over the nickel/nickel oxide catalyst bed material.

Alternatively, hydrogen can be introduced directly into the catalyst bed comprising the catalyst bed material according to the invention separately and downstream from the olefin-containing hydrocarbon feedstock introduction. This has the advantage that by injecting the hydrogen in the catalyst bed downstream from the introduction of the feedstock, the catalyst bed material can act more predominantly as a sorbent material, ad- and/or absorbing other known impurities from the olefin-containing hydrocarbon feedstock. The injection of hydrogen occurs preferably at least a quarter of the way down the bed, more preferably at least half way down the bed, even more preferably three-quarters of the way down the bed. The sorption of impurities such as carbonyl sulphide, arsine, antimony compounds such as antimony hydride, and carbon monoxide using nickel/nickel oxide materials according to the invention is known (See EP 0 308 569, GB 2162194, GB 2242199, EP 0 648 720 and EP 2 006 011) and will occur more predominantly upstream of the hydrogen injection point. The amount and proportion of hydrogen to be introduced is the same as described above for the case where hydrogen is introduced into the hydrocarbon feedstock stream.

The invention also covers the possibility of introducing hydrogen into the olefin-containing hydrocarbon feedstock prior to passing it over the catalyst bed material and simultaneously directly into the catalyst bed comprising the catalyst bed material downstream from the introduction of the hydrocarbon feedstock.

The hydrocarbon feedstock is passed over the nickel/nickel oxide catalyst bed material at a temperature of from −10° C. to 80° C., preferably of from 0° C. to 40° C., more preferably from 0° C. to 30° C., more preferably from 0° C. to 25° C., even more preferably 0° C. to 20° C. and at a liquid hourly space velocity (LHSV) of from 0.1 to 60 l/l·h, namely of from 5, 10, 20, 25, 30, 35 or 40 up to 45, 50, 55 or 60 l/l·h, preferably at a LHSV of from 20 to 60 l/l·h, more preferably of from 20 to 40 l/l·h, and most preferably at about 30 l/l·h. It is surprising that still even at temperatures as low as 0° C. to 30° C., more preferably up to 25° C. and even more preferably up to 20° C., most preferably around 20° C. and at LHSVs of from 20 to 40 l/l·h, up to 50 l/l·h and even up to 60 l/l·h, but in particular at around 20 to 30 l/l·h, most preferably around 20 l/l·h the invention can still be rapidly carried out due the high liquid hourly velocities of the propylene that can be employed. Such relatively high liquid hourly space velocities can be used to make up for small catalyst bed volumes i.e. small vessels or driers containing the catalyst bed material. At these conditions, other impurities as mentioned above will also be removed during the hydrogenation process.

If carrying out the process with a propylene-containing feedstock, the pressure used is generally such as to retain the feedstock in the liquid phase.

Once spent, the catalyst bed material can be partially reactivated by treatment with inert gas at elevated temperatures and optionally in the presence of hydrogen.

In one embodiment of the present invention, the recovered feedstock can be passed over a second catalyst bed material if it is required that the olefin-containing hydrocarbon feedstock be substantially free of hydrogen for subsequent utilisation. The second catalyst bed material can be any material, which is known to ab- or adsorb or convert hydrogen, for example hydrogenation catalysts comprising palladium or platinum. Preferably, the second catalyst bed material is the same as the first catalyst bed material i.e. comprising nickel deposited on a support material wherein said nickel is present as both nickel oxide and metallic nickel, since this material is more economical and more selective than other known hydrogenation catalysts. Of course, this second purification step is preferably carried out without any additional introduction of hydrogen. This second catalyst bed is shown in FIG. 1. In a preferred embodiment the purification process can be carried out in one mode using only the first bed 1 in the presence of hydrogen, in a second mode using only the second bed 2 or a third mode using both the first and second beds 1 and 2.

The process according to the invention also covers the possibility of passing the olefin-containing hydrocarbon feedstock over additional materials upstream to passing it over the first catalyst bed material of the invention. These can act as guard beds, pretreating the propylene by removing various impurities e.g. water, carbonyl sulphide, arsine, antimony compounds such as antimony hydride, and carbon monoxide, thereby increasing the nickel/nickel oxide catalyst bed material's overall lifetime. Examples of such optional additional sorbent materials are metal oxides such as copper oxide, zinc oxide, zirconium oxide or manganese oxide, aluminas (including promoted aluminas), palladium, platinum, and molecular sieves such as 3A, 4A, 5A or 13X, as well as copper/copper oxide sorbents. Preferably, molecular sieve 13X is used, because of its larger pore size. Alternatively or additionally, the feedstock can be passed over a sorbent material identical to the first catalyst bed material i.e. comprising the metallic nickel and nickel oxide, but in the absence of additional hydrogen. As explained above, the nickel/nickel oxide material can also act as a sorbent, ad- and/or absorbing other known impurities from the olefin-containing hydrocarbon feedstock.

In view of utilising the latest generation of metallocene-type catalysts in the production of polypropylene and polyethylene, the olefin-containing hydrocarbon feedstock preferably contains less than 5 ppm, more preferably less than 1 ppm and most preferably in the ppb range of acetylenics and allenes (in particular propadiene). The process of the present invention is capable of reducing the concentration of these impurities to the desired level. The total concentration of such impurities to use the process according to the invention may be as high as 100 ppm or higher, depending on the process used to produce the original feedstock.

Furthermore, it has been found that the olefin-containing hydrocarbons purified according to the present invention, result in higher catalyst productivity during polymerisations, in particular metallocene-catalysed polymerisations. This results in a considerable reduction in the amount of required catalyst. In addition, the catalyst productivities remain more constant, allowing for better control over the polymer products and more stable melt flow indices. Furthermore, stable polymerisation reactor conditions can be achieved, such that blockages become less frequent and unnecessary reactor shutdown is avoided.

The examples, which follow, are given to provide a better illustration of the process of the present invention. These examples should not, however, be construed as limiting the scope of the invention as there are many variations which may be made thereon, as those skilled in the art will recognise.

EXAMPLES

Example 1 (Propylene Purification in a Single Metallic Nickel/Nickel Oxide Bed)

Hydrogen was introduced into a liquid feedstock of polymer grade propylene containing 39 ppm of MAPD (28 ppm mol methylacetylene and 11 ppm mol propadiene). The feedstock was then passed in the upflow mode at a feed rate of 510 g/h over a catalyst bed material comprising metallic nickel/nickel oxide deposited on a silica-alumina support in bed 1 having the following properties:
  a weight ratio of metallic nickel to nickel oxide of 0.5 and
    a total weight of metallic nickel and nickel oxide being 50% of the weight of the catalyst bed material
  specific surface area of 150 m$^2$/g
  bulk density of 0.80 g/cm$^3$
  shaped as 1/16" extrudates The hydrogen flow into the propylene feedstock was steadily increased from 1 to 10 Nl/h. The feedstock was passed over the catalyst bed material at a temperature of 20° C., under a pressure of 17 barg, and an LHSV of 20 l/l·h. Thus, 5000 ppm mol of hydrogen was required in order to substantially hydrogenate the MAPD in the feedstock. Results are provided in Table I.

TABLE I

| Composition | Initial propylene feedstock | Recovered propylene feedstock | Conversion in mol % |
|---|---|---|---|
| Propylene [wt. %] | 98.3 | 97.9 | 0.4** |
| Propadiene [ppm mol]* | 11 | 0 | 99.0 |
| Methylacetylene [ppm mol]* | 28 | 0 | 99.6 |
| Hydrogen [ppm mol] | 0 | 10520 | 39.5 |

*detection limit <20 ppb
**propylene hydrogenated to propane

From Table I, it can be seen that MAPD was successfully selectively hydrogenated using the nickel/nickel oxide catalyst bed material. The small amount of propylene converted into propane i.e. 0.4 mol % is acceptable, since the purified propylene feedstock can now be used for catalytic polymerisations with a reduced risk of reactor shutdown.

Example 2 (Propylene Purification in Two Nickel/Nickel Oxide Beds in Series)

Hydrogen was introduced into a liquid feedstock of polymer grade propylene containing 10 ppm of MAPD (7 ppm mol methylacetylene and 3 ppm mol propadiene). The feedstock was then passed in the upflow mode at a feed rate of 765 g/h over a first catalyst bed material in bed 1, having the same properties as the catalyst bed material in Example 1, followed by an identical second catalyst bed material in bed 2 at a feed rate of 688 g/h. This system is illustrated in FIG. 1.

The feedstock was passed over both catalyst bed materials at a temperature of 20° C., under a pressure of 17 barg, and an LHSV of 20 l/l·h. In order to substantially hydrogenate the MAPD in the feedstock, 7000 ppm mol of hydrogen was required. Results of the propylene feedstock recovered from bed 2 are provided in Table II.

TABLE II

| Composition | Initial propylene feedstock | Recovered propylene feedstock (outlet bed 2) | Conversion in mol % |
|---|---|---|---|
| Propylene [wt. %] | 97.82 | 97.07 | 0.8** |
| Propadiene [ppm mol]* | 3 | 0.2 | 93.30 |
| Methylacetylene [ppm mol]* | 7 | 0.4 | 94.30 |
| Hydrogen [ppm mol] | 0 | 14 | 99.80 |

*detection limit <20 ppb
**propylene hydrogenated to propane

The invention claimed is:

1. A process for purifying an olefin-containing hydrocarbon feedstock comprising:
    passing the olefin-containing hydrocarbon feedstock in the presence of hydrogen over a first catalyst bed material consisting of nickel deposited on a support material wherein said nickel is present as both nickel oxide and metallic nickel, wherein the weight ratio of metallic nickel to nickel oxide is from 0.4 to 2.0, with the provision that the metallic nickel represents neither less than 6 wt. %, nor more than 50 wt. % of the first catalyst bed material, and the first catalyst bed material consists of from 40 to 70 wt. % of the nickel and from 30 to 60 wt. % of the support material;
    recovering the olefin-containing hydrocarbon feedstock having a substantially reduced acetylenics and allenes content.

2. The process according to claim 1, wherein the total weight of nickel oxide and metallic nickel represents from 45 to 55 wt. % of the first catalyst bed material, and the first catalyst bed material includes 45 to 55 wt. % of the support material.

3. The process according to claim 1, wherein the weight ratio of metallic nickel to nickel oxide is from 0.4 to 1.0.

4. The process according to claim 1, wherein said first catalyst bed material has a specific surface area from 10 to 400 m$^2$/g.

5. The process according to claim 1 wherein the hydrogen is introduced into the olefin-containing hydrocarbon feedstock before passing said olefin-containing hydrocarbon feedstock over the first catalyst bed material.

6. The process according to claim 1 wherein all of the hydrogen is introduced into a catalyst bed comprising the first catalyst bed material at an injection point downstream from the introduction of the olefin-containing hydrocarbon feedstock, wherein upstream of the injection point of the hydrogen the first catalyst bed material acts predominately as a sorbent material, and wherein downstream of the injection point of the hydrogen the first catalyst bed material catalyzes the conversion of acetylenics and allenes into olefins.

7. The process according to claim 1 further comprising passing the recovered olefin-containing hydrocarbon feedstock over a second catalyst bed material downstream from the first catalyst bed material to substantially remove all of the hydrogen.

8. The process according to claim 7 wherein the second catalyst bed material is the same as the first catalyst bed material.

9. The process according to claim 1, wherein the olefin-containing hydrocarbon feedstock comprises more than 75 wt. % of propylene.

10. The process according to claim 1, carried out at a temperature of from −10° C. to 80° C. and at a liquid hourly space velocity (LHSV) from 0.1 to 60 l/l·h.

11. The process according to claim 1, wherein the olefin-containing hydrocarbon feedstock comprises up to 100 parts per million (ppm) of acetylenics and allenes.

12. The process according to claim 1, wherein the recovered olefin-containing hydrocarbon feedstock comprises less than 500 parts per billion (ppb) of acetylenics and allenes.

13. The process according to claim 1, wherein upstream of the first catalyst bed material, the olefin-containing hydrocarbon feedstock is passed over one or more of the following:
    molecular sieves chosen from one or more of 3A, 4A, 5A or 13X;
    activated alumina.

14. The process according to claim 1, wherein the first catalyst bed material comprises spherical particles having particle diameters that do not exceed about 3.5 mm.

15. The process according to claim 1, wherein the first catalyst bed material comprises cylindrical particles having particle diameters of from 1 to 2 mm and lengths of from 3 to 8 mm.

16. The process of claim 1, wherein a molar ratio of hydrogen to acetylenics and allenes within the olefin-containing hydrocarbon feedstock ranges from 1 to 1500.

17. The process of claim 1, wherein the nickel is deposited onto the support material and then the nickel deposited on the support material is only partially reduced to form the metallic nickel, wherein non-reduced nickel comprises the nickel oxide.

18. The process of claim 1, wherein the metallic nickel comprises crystallites having a size ranging from 1 nm to 100 nm.

19. The process of claim 16, wherein the molar ratio of hydrogen to acetylenics and allenes within the olefin-containing hydrocarbon feedstock ranges from 178 up to 1500.

20. A process for purifying an olefin-containing hydrocarbon feedstock comprising:

passing the olefin-containing hydrocarbon feedstock in the presence of hydrogen over a first catalyst bed material consisting of nickel deposited on a support material wherein said nickel is present as both nickel oxide and metallic nickel, wherein the weight ratio of metallic nickel to nickel oxide is from 0.4 to 2.0, with the provision that the metallic nickel represents neither less than 6 wt. %, nor more than 50 wt. % of the first catalyst bed material, and the first catalyst bed material consists of from 10 to 80 wt. % of the nickel and from 20 to 90 wt. % of the support material;

recovering the olefin-containing hydrocarbon feedstock having a substantially reduced acetylenics and allenes content.

21. The process of claim 20, further comprising forming the first catalyst bed material by:

forming a solution by dissolving nickel nitrate in water;
mixing the solution with the support material;
precipitating the nickel;
washing, drying and calcining the precipitate; and
partially reducing the nickel by means of hydrogen to form the metallic nickel.

22. The process of claim 21, further comprising conditioning the first catalyst bed material prior to contact with the olefin-containing hydrocarbon feedstock by passing an inert gas flow containing a minor amount of at least one light olefin in a concentration of from 0.1 to 5 vol % over the first catalyst bed material.

23. The process of claim 1, further comprising conditioning the first catalyst bed material prior to contact with the olefin-containing hydrocarbon feedstock by passing an inert gas flow containing a minor amount of at least one light olefin in a concentration of from 0.1 to 5 vol % over the first catalyst bed material.

* * * * *